(12) United States Patent
Rosevear et al.

(10) Patent No.: US 8,755,491 B2
(45) Date of Patent: Jun. 17, 2014

(54) RISE/FALL TIME CONTROL FOR X-RAY PULSES

(75) Inventors: Thomas William Rosevear, Liverpool, NY (US); Oscar Khutoryansky, Mashpee, MA (US); Yevgeny Maltsev, Hudson, MA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 409 days.

(21) Appl. No.: 13/259,943

(22) PCT Filed: Mar. 29, 2010

(86) PCT No.: PCT/US2010/029035
§ 371 (c)(1),
(2), (4) Date: Dec. 6, 2011

(87) PCT Pub. No.: WO2010/111697
PCT Pub. Date: Sep. 30, 2010

(65) Prior Publication Data
US 2012/0170717 A1    Jul. 5, 2012

Related U.S. Application Data

(60) Provisional application No. 61/163,895, filed on Mar. 27, 2009.

(51) Int. Cl.
*H05G 1/24*    (2006.01)
(52) U.S. Cl.
CPC ..................... *H05G 1/24* (2013.01)
USPC ............................................. 378/103
(58) Field of Classification Search
CPC ..................................... H05G 1/24
USPC ............. 378/101, 103, 102, 108, 110–114
See application file for complete search history.

(56) References Cited

U.S. PATENT DOCUMENTS

| 4,039,812 | A | | 8/1977 | Grassmé et al. |
| 4,234,862 | A | | 11/1980 | Prevotat |
| 4,317,039 | A | | 2/1982 | Romandi |
| 4,322,625 | A | * | 3/1982 | Daniels et al. ............... 378/110 |
| 4,419,648 | A | | 12/1983 | Seipel |

(Continued)

FOREIGN PATENT DOCUMENTS

| JP | 55-138215 | 10/1980 |
| JP | 2001-135531 | 5/2001 |

(Continued)

*Primary Examiner* — Irakli Kiknadze
(74) *Attorney, Agent, or Firm* — Vista IP Law Group, LLP

(57) ABSTRACT

A method for generating a fast rise-time X-ray pulse includes the steps of providing an n-phase x-ray generator, the x-ray generator including an n-phase transformer having at least one primary winding and at least one secondary winding per phase, and providing n sections of rectifiers, each rectifier having at least a fast pulse rise-time mode and a n-phase ripple flat-top mode. According to the method, at least a first capacitor is charged in each of the n sections of rectifiers at a ripple of less than n-phases to create a fast leading edge of the fast rise-time pulse, and at least a second capacitor is charged in each of the n sections or rectifiers at an n-phase ripple to create a substantially flat-top of the fast rise-time pulse.

8 Claims, 14 Drawing Sheets

(56) References Cited

U.S. PATENT DOCUMENTS

| | | |
|---|---|---|
| 4,876,634 A | 10/1989 | Paice |
| 4,930,059 A | 5/1990 | Rutt |
| 5,210,930 A | 5/1993 | Watabe et al. |
| 5,231,564 A * | 7/1993 | Pellegrino et al. ............... 363/61 |
| 5,463,668 A | 10/1995 | Kagaya |
| 6,340,851 B1 | 1/2002 | Rinaldi et al. |
| 6,577,510 B1 | 6/2003 | Yasumura |
| 6,587,358 B1 | 7/2003 | Yasumura |
| 6,687,137 B1 | 2/2004 | Yasumura |
| 6,914,509 B2 | 7/2005 | Yu et al. |
| 2002/0033748 A1 | 3/2002 | Bolotinsky et al. |
| 2002/0054659 A1 | 5/2002 | Okumura et al. |
| 2003/0062980 A1 | 4/2003 | Scheible et al. |
| 2003/0206087 A1 | 11/2003 | Raff |
| 2006/0077028 A1 | 4/2006 | Huang |

FOREIGN PATENT DOCUMENTS

| | | |
|---|---|---|
| JP | 2005-265620 | 9/2005 |
| SU | 853679 | 8/1981 |
| SU | 1078476 | 3/1984 |
| SU | 1337925 | 9/1987 |
| SU | 1390648 | 4/1988 |
| SU | 1658223 | 6/1991 |
| SU | 1714697 | 2/1992 |

* cited by examiner

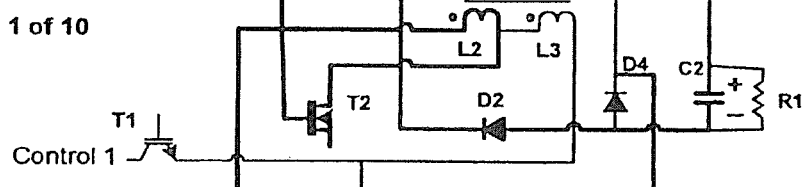
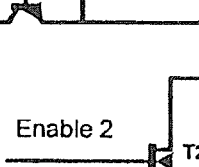
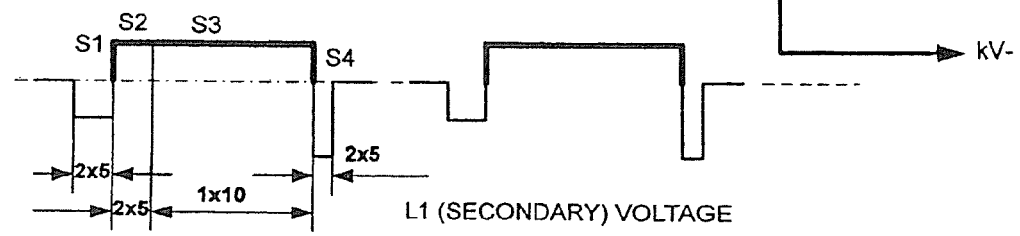
FIG. 9
Step 4
Section 1 of 10
Section 2 of 10
Section 3 of 10
Section 4 of 10
Section 9 of 10
Section 10 of 10

FIG. 10
Step 5
Section 1 of 10
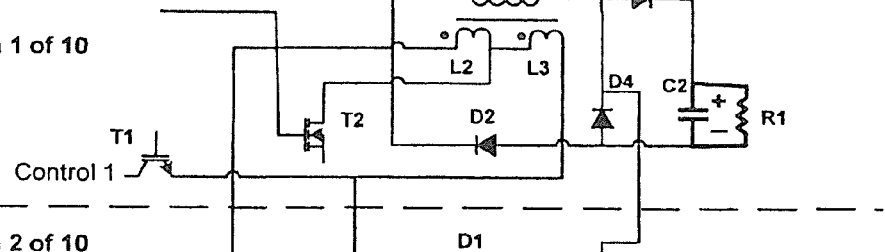
Section 2 of 10
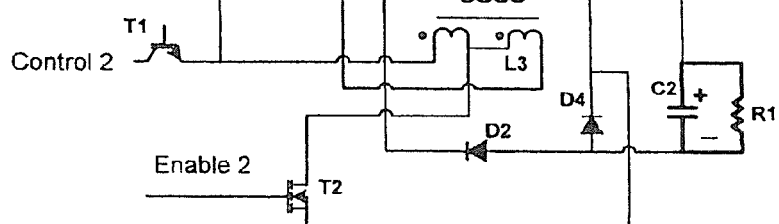
Section 3 of 10
Section 4 of 10
Section 9 of 10
Section 10 of 10
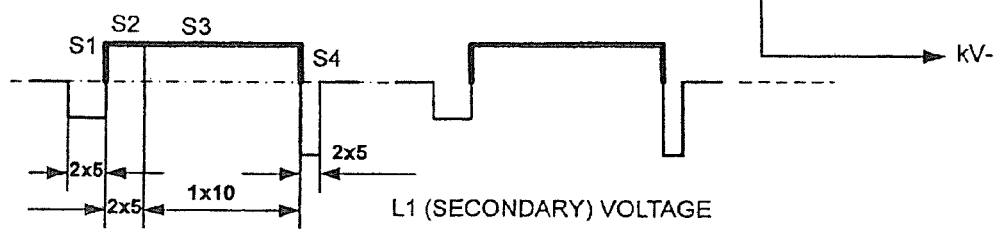

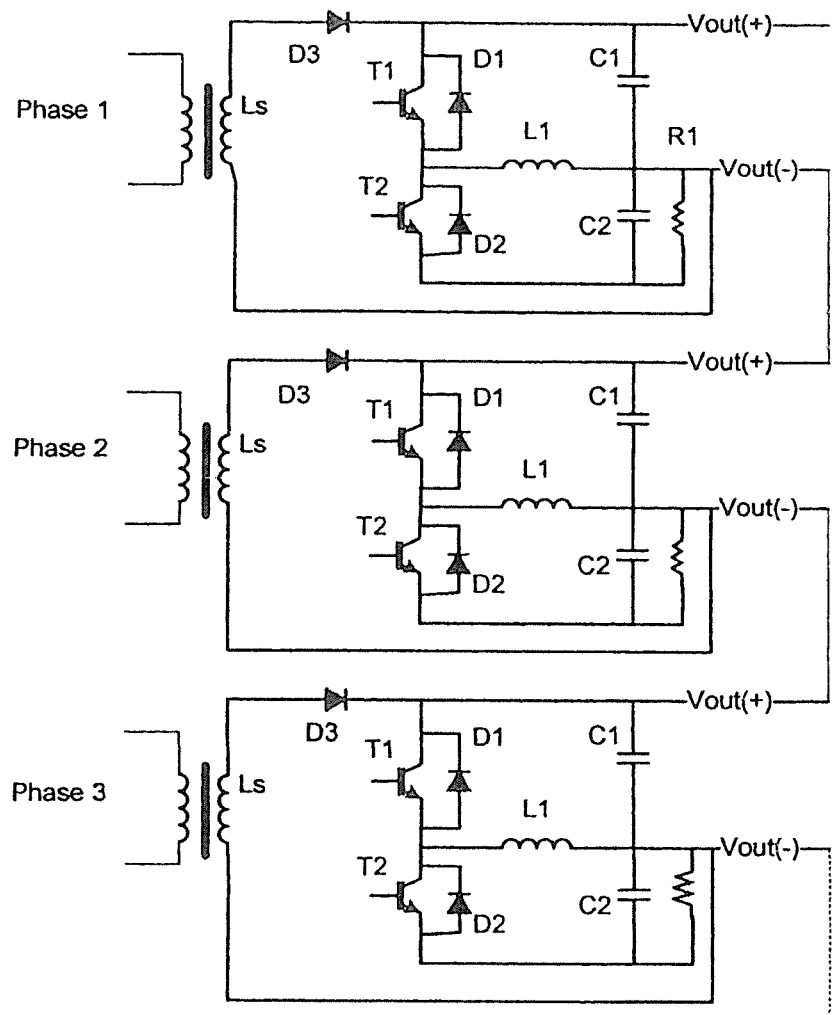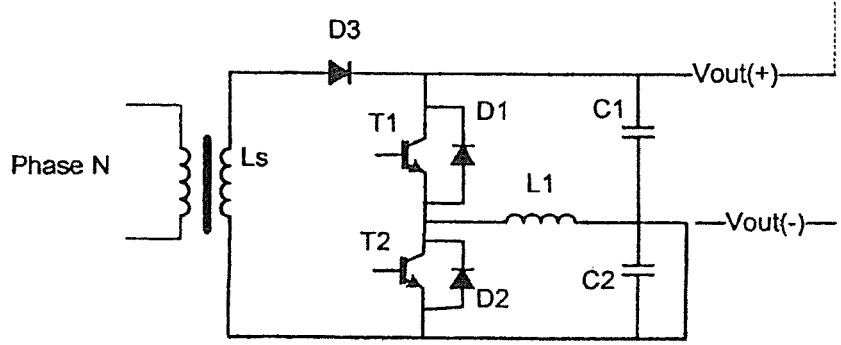
FIG. 17

RISE/FALL TIME CONTROL FOR X-RAY PULSES

CROSS-REFERENCE TO RELATED APPLICATIONS

This application is a national phase patent application pursuant to 35 U.S.C. §371 based upon PCT Application No. PCT/US2010/029035, filed Mar. 29, 2010, which claims priority of provisional application U.S. Ser. No. 61/163,895, filed Mar. 27, 2009 pursuant to 35 U.S.C. §119, the entire contents of which are herein incorporated by reference. Reference is further made to co-pending U.S. patent application Ser. No. 12/275,679, filed Nov. 21, 2008, entitled "3D POLYPHASE TRANSFORMER" and provisional patent application, U.S. patent application Ser. No. 61/044,770, filed Apr. 14, 2008, entitled "3D POLY-PHASE TRANSFORMER", the entire contents of each herein being incorporated in their entirety.

FIELD OF THE INVENTION

This invention relates generally to an x-ray generator and more particularly to an x-ray generator that generates x-ray impulses, each impulse having a fast rise time and a fast fall time.

BACKGROUND OF THE INVENTION

X-ray generators are used to generate an electrical power pulse (i.e. an x-ray impulse) to cause an x-ray tube to emit x-rays in short bursts (impulses). In medical applications, there is increasing need for better well defined x-ray impulses. For example, with an increasing awareness of the risks associated with exposure to x-rays, it is highly desirable to limit patient x-ray exposure to the shortest time practical to achieve a desired x-ray diagnostic image.

As is well known, as the voltage across an x-ray tube increases during the leading edge of an x-ray impulse, at some threshold voltage, the tube begins to emit x-rays at an energy level, typically expressed in kilovolt electron volts ("keV"). At some voltage level of the leading edge of the x-ray impulse (related to the x-ray impulse rise time), typically at about 90% of the desired x-ray tube voltage, the x-ray radiation is useful and contributes to the desired exposure. Similarly, on the falling edge of the x-ray impulse (related to the x-ray impulse fall time), below about 90% of the desired x-ray tube voltage to about the threshold voltage, there is still x-ray emission, however at energy levels too low to be useful for the desired exposure. The x-rays emitted that have too low an energy to be useful to the desired diagnostic image, while they increase patient's radiation dose, are called "soft x-rays".

"Crow-bar" circuits have been used in prior art x-ray apparatus to cause a faster falling edge of an x-ray impulse. A crow-bar circuit literally short circuits the output of the x-ray generator at the end of a desired x-ray impulse, thus more quickly discharging both the output capacitors of the x-ray generator and any charge stored in the distributed capacitance of the length of cable from the x-ray generator to the x-ray tube. Crow-bar circuits are both inefficient, because they waste any remaining stored energy as heat, as well as reduce the useful life of many x-ray generator electronic components since high peak currents associated with operation of a crow-bar are generally destructive to any components in the high current path.

Another problem is that a significant amount of stored energy in x-ray generator circuits is typically damped through discharge components and wasted as heat.

What is needed is an x-ray generator that can generate x-ray impulses having faster rise and fall times to minimize patient exposures to soft x-rays. What is also needed is a more efficient x-ray generator that can generate x-ray impulses having faster rise and fall times while minimizing wasted heat energy.

SUMMARY OF THE INVENTION

According to a one version, there is provided an X-ray generator for generating a fast rise-time pulse, the generator comprising an n-phase poly-phase transformer having at least one primary winding and at least one secondary winding per phase. N rectifier circuits are each coupled electrically to each of the secondary windings per phase, each of the n rectifier circuits comprising at least one capacitor electrically coupled to at least a first rectifier and in which the first rectifier is disposed between the at least one secondary winding and the first capacitor and configured to provide a fast rise time of a leading edge of a fast rise time pulse. The rectifier circuits each further include at least a second rectifier electrically disposed between the at least one secondary winding and the second capacitor and configured to provide a filtered n-phase pulse flat-top. The generator further includes at least n active control switches, each of the control switches being electrically coupled to at least one primary winding and configured to set a selected one of rectifier mode: 1) a fast pulse rise-time mode and 2) a flat-top low ripple mode. Each of the first capacitors is charged by a rectified ripple of less than n at or before a leading edge of the fast rise-time pulse and each of the second capacitors is configured to operate with an n-phase ripple to provide a substantially flat pulse flat top of the fast rise-time pulse.

In one embodiment, both the first capacitor and the second capacitor are pre-charged before the leading edge of the fast rise-time pulse.

A peak pulse amplitude of the fast rise-time pulse can be generated by a series combination of a plurality of rectified voltages, each one of the rectified voltages being output from each of the n-rectifiers.

According to another version, there is provided a method for generating a fast rise-time X-ray pulse, the method comprising the steps of: providing an n-phase, X-ray generator including an n-phase transformer having at least one primary winding and at least one secondary winding per phase, providing n sections of rectifiers, each rectifier having at least a fast rise-time pulse mode and a n-phase ripple flat-top mode. According to this method, a first capacitor is charged in each of the n sections of rectifiers at a ripple of less than n-phases to create a fast leading edge of the fast rise-time pulse and a second capacitor is charged in each of n sections of rectifiers at an n-phase ripple to create a substantially flat-top of the fast rise-time pulse.

In one instance, the first capacitor is pre-charged prior to the step of charging the first capacitor. In at least one other instance, the second capacitor is pre-charged before the step of charging the first capacitor.

According to another version, the first capacitor is discharged to create a fast fall time of a falling edge of the fast rise-time pulse after the step of charging the second capacitor. According to another version, the second capacitor is discharged after the second capacitor is charged.

These and other features and advantages will be readily apparent from the following Detailed Description, which should be read in conjunction with the accompanying drawings.

BRIEF DESCRIPTION OF THE DRAWINGS

For a further understanding of these and other described features, reference will be made to the following Detailed Description which is to be read in connection with the accompanying drawings, in which:

FIG. 9 shows a schematic diagram of FIG. 3 emphasizing the current path in step 4 of the circuit operation;

FIG. 10 shows a schematic diagram of FIG. 3 emphasizing the current path in step 5 of the circuit operation;

FIG. 17 shows a schematic diagram of a poly-phase transformer design having multiple circuit sections according to FIG. 12;

It should be noted that the drawings are not necessarily to scale, emphasis instead generally being placed upon illustrating the principles of the invention described herein. In the drawings, like numerals are used to indicate like parts throughout the various views for purposes of clarity.

DETAILED DESCRIPTION

The invention generally pertains to circuit topologies that can create fast x-ray impulse fall times in single phase and poly phase x-ray generator applications. In some poly phase x-ray generator applications, the new circuit topologies can produce both fast pulse rise and pulse fall times as well as a pulse with a substantially low ripple pulse flat-top. In both single phase and poly-phase x-ray generator applications, the new circuits can replace prior art crow-bar circuits, which, as described above, are energy wasteful and can stress both passive and active x-ray generator components. Additional applications of the fast pulse circuit topologies described herein include, but are not limited to, laser beam generators, high voltage controls, such as high voltage controls with applications in nuclear physics, and high power signal generators, such as high power signal generators used to generate FFT waveforms.

In part I of this description, a single section of one embodiment of the new circuits is described where the circuit can function both as the x-ray generator normal rectifier, as well as replacing a crow-bar circuit of the prior art to create fast x-ray generator pulse fall times. In part II of this description, a poly-phase embodiment is described that can generate both fast pulse rise and pulse fall times as well as a pulse with a substantially low ripple pulse flat-top. Part III describes another embodiment of a new circuit section, a fast pulse x-ray generator active rectifier with energy re-use. Part IV describes an exemplary x-ray generator that uses the new x-ray generator circuit, and part V presents a summary.

Figure 1:
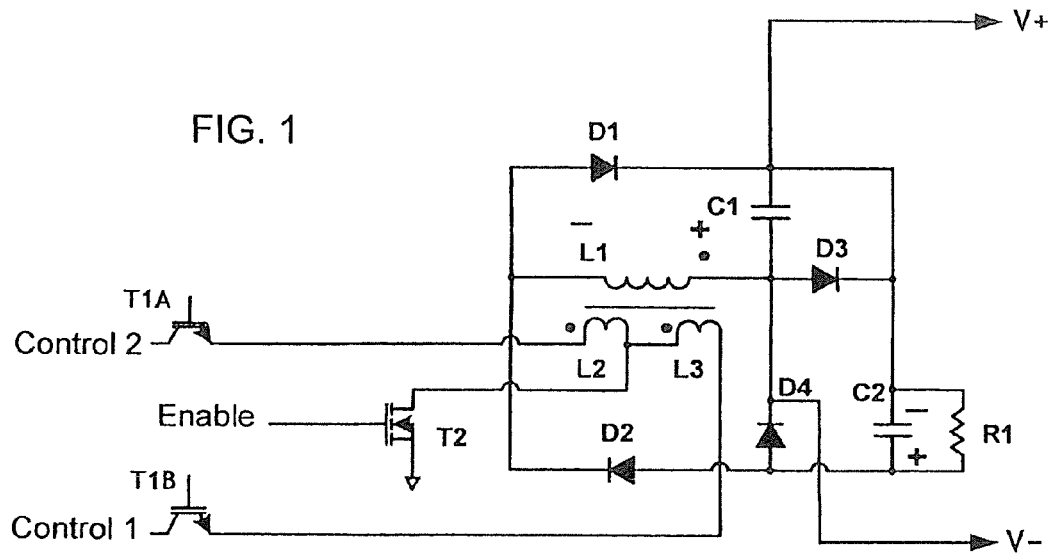
FIG. 1 shows an exemplary schematic diagram of a single section of a new x-ray circuit.

Part I, Single Section Circuit Topology:

FIG. 1 shows one exemplary schematic diagram of a single section of the new circuit. The features and operation of the exemplary single section of FIG. 1 are now described as follows.

Enable/Disable:

Each section, as shown in FIG. 1, can be enabled or disabled. One reason to provide the enable function is to ensure that a given section is secured in an "OFF" mode for radiation safety reasons (thus ensuring there will not be an accidental or unintentional powering of an associated x-ray tube). Another reason to enable/disable a given section will be seen below, where in poly-phase operation, there can be intervals where a give section is not utilized during pulse cycle.

Control (Input Electrical Power):

Electrical power is input to the circuit typically as a stream or train of electronic pulses via a "control" input or inputs. In a first embodiment of a section as shown in FIG. 1, there can be positive pulse applied to either control 1 or to control 2.

Note that in some embodiments, a bipolar pulse source can provide either positive going or negative going pulses. Or, as shown in the simplified schematic diagram of FIG. 2, control signals, typically pulse trains, can be generated as either positive or negative pulses by use of polarity selection switches S1-S4. S1-S4 are representative of known techniques for generating positive or negative pulses using a combination of electronic switches and passive components as needed for biasing, current limiting, impedance matching, etc.

Figure 2:
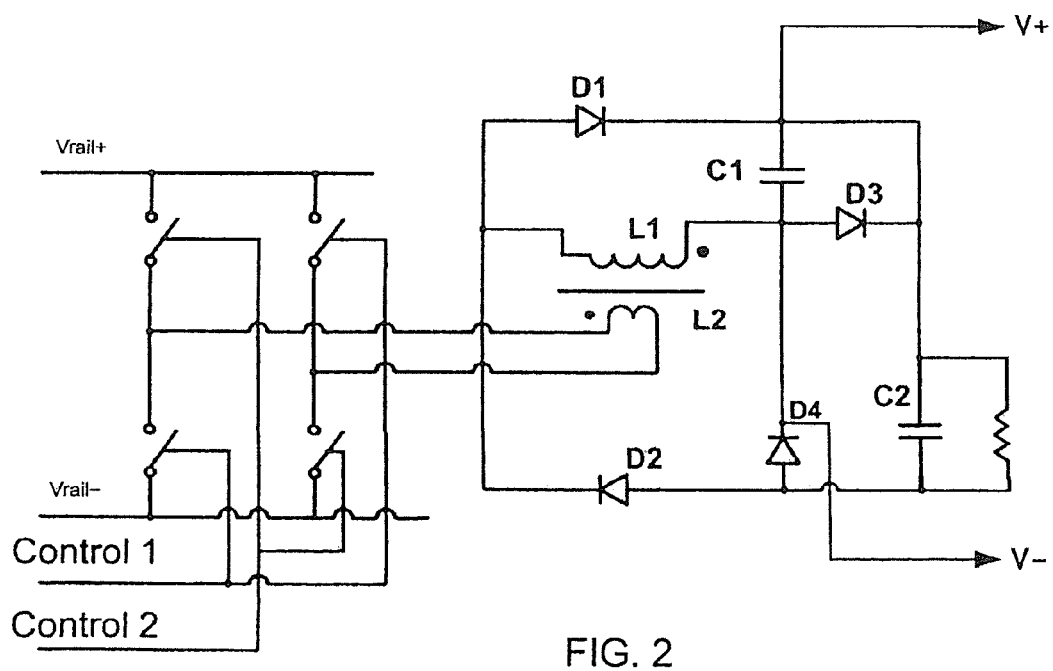
FIG. 2 shows a simplified schematic diagram of the circuit section of FIG. 1 controlled by bipolar control signals.

Note that pulses at control 1 of FIG. 1 correspond to positive pulses in the embodiment of FIG. 2 (e.g. S2 and S3 closed, while S1 and S4 are open), and that pulses at control 2 of FIG. 1 correspond to negative control pulses in the embodiment of FIG. 2 (e.g. S1 and S4 closed, while S2 and S3 are open). One advantage of the embodiment of FIG. 1 regarding input electrical power, is that the input pulse circuits can be somewhat reduced in complexity compared to the embodiment of FIG. 2, in part, because the input circuits are unipolar. On the other hand, one advantage of the embodiment of FIG. 2, regarding input electrical power, is that only one primary coil per section is used, thus slightly simplifying construction of the transformer, as compared to the embodiment of FIG. 1 that uses either two primary windings or a tapped primary winding with three connecting wires.

Circuit Operation:

Following a brief list of components of a single exemplary circuit section, circuit operation of a single section is described in more detail.

Referring to FIG. 1, the components of the exemplary single section of the circuit include:

L1: Secondary winding of a transformer
L2, L3: Primary windings of a transformer
C1: HV filtering capacitor.
C2: Discharge assistance capacitor.
D1, D2: Rectifiers (typically diodes)
D3: Discharging assistance rectifier (typically a diode)
D4: Charge balancing rectifier (typically a diode)
T1, Control transistor (e.g. an insulated gate bipolar transistor ("IGBT"))
T2: Enable transistor (e.g. a field effect transistor ("FET"))

Each step in the circuit operation of a circuit section has associated with it a specific aspect of the operation of the circuit and a specific current path through the rectifiers of on the secondary side L1 of the transformer which includes windings L1, L2, and L3 in FIG. 1 (L1 and L2 in FIG. 2). There are several steps of circuit operation that occur in time, beginning before an x-ray impulse is desired and ending after the falling edge of the x-ray impulse. The sequencing or order of the control steps yields the desired x-ray impulse characteristics.

One aspect of the circuit operation is that the current paths through the rectifiers in the secondary circuit on the secondary side of the transformer are controlled by the primary circuit which is galvanically isolated from the secondary circuit by the transformer. The circuit control (selection of secondary rectifier paths) is accomplished both by selecting which control line to power on the primary side (control 1 and control 2 in FIG. 1) or by which polarity of control pulse is used (control in FIG. 2). Note that a single section of either of the circuit topologies of FIG. 1 or FIG. 2 can achieve a fast x-ray impulse fall time (e.g. with a single phase power source). Typically a fall time achieved by just one section is faster than can be achieved with a comparable prior art crowbar circuit. As described below in part II, further improvements including a low ripple x-ray impulse flat-top and fast x-ray impulse rise time can be achieved using multiple sections in a poly-phase circuit topology.

Part II, Multiple Section Poly-Phase Circuit Topology:

Several embodiments of a poly-phase x-ray generator were described in co-pending U.S. patent application Ser. No. 12/275,679, filed Nov. 21, 2008, entitled "3D POLY-PHASE TRANSFORMER", by the same inventors and also assigned to the Infimed Corporation, the 12/275,679 application being incorporated herein in its entirety. The new x-ray generator single circuit topology (single section) as described above is now applied to a poly-phase transformer based x-ray generator. The poly-phase transformer can be, for example, of the type described in the co-pending Ser. No. 12/275,679 application.

Poly-phase operation has some similarity to the circuit operation described above for a single circuit section (e.g. a fast falling edge). However in a poly-phase application, there can be additional benefits including a faster x-ray impulse rise time as well as an x-ray impulse fast fall time, and a lower ripple amplitude pulse flat-top. In poly-phase operation using multiple circuit sections, the control pulses can be provided in various phase combinations. For example, there can be effectively single phase operation across all sections (control pulses of each section in phase with each other), control pulses staggered in time, yet also overlapping in duration, or control pulses staggered in time and not overlapping (e.g. spaced in phase and related to the number of phases of the poly-phase transformer).

Figure 3:
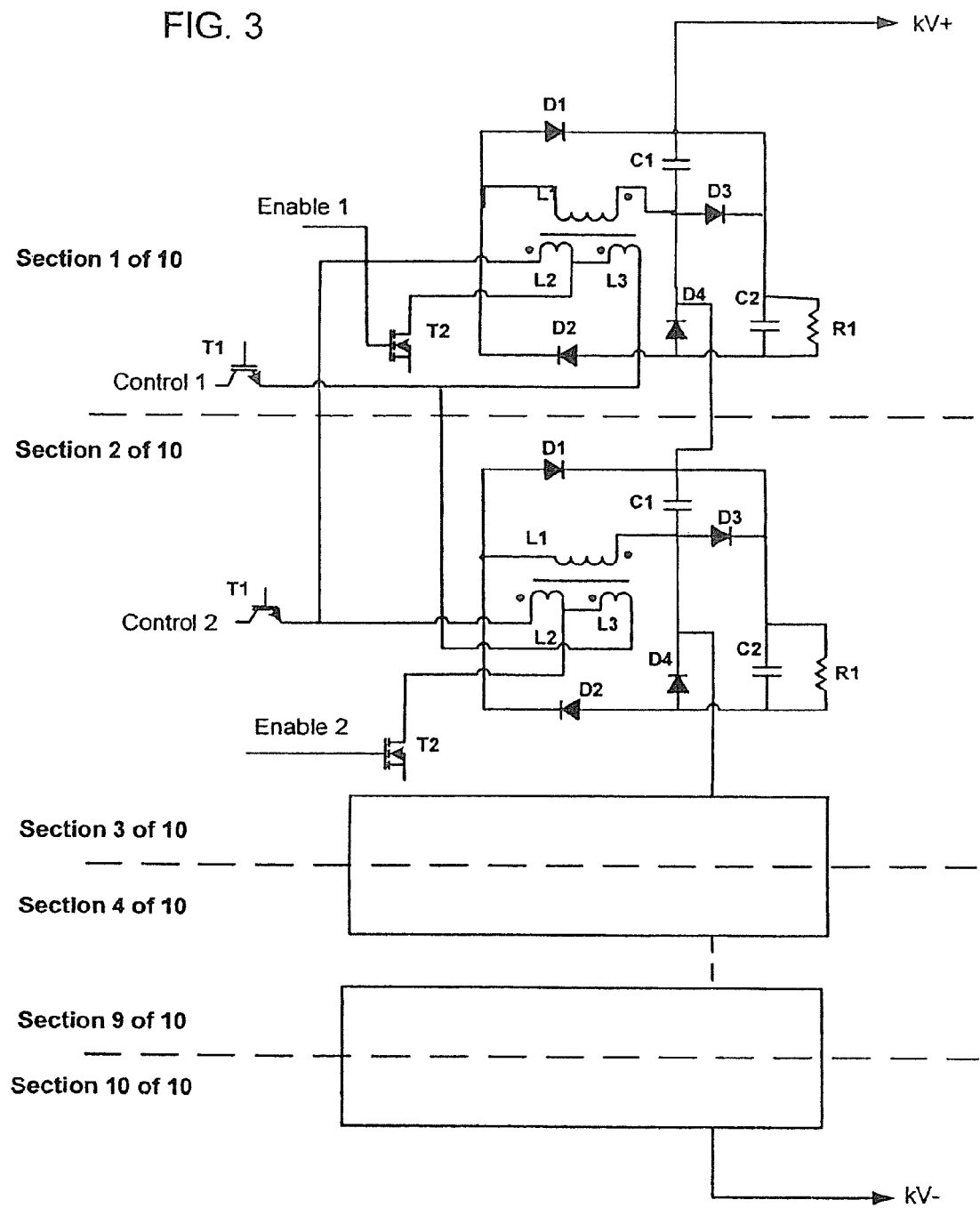
FIG. 3 shows a schematic diagram of one exemplary embodiment of a poly-phase x-ray generator employing the x-ray circuit of FIG. 1.

Turning to FIG. 3, one exemplary embodiment of multiple section poly-phase operation is now described in more detail. In this example, there are 10 sections of the circuit described above corresponding to a 10 phase poly-phase transformer. In the description of the steps which follow, FIG. 3 has been redrawn in successive drawings (FIG. 5 to FIG. 10) with thick lines to emphasize particular current paths as described below. Note that in the exemplary operation of one poly-phase embodiment as described below in FIG. 5 to FIG. 10, parameters such as the number of participating phases, their sequencing, and operating frequency are provided as a working example only. As will be appreciated by those skilled in the art, there can be variations of such parameters.

In this exemplary sequence of operation, there are total 5 steps of operation (1, 2, 3a/3b, 4, and 5) in a control sequence from 1 to 5. Step 3 is divided into steps 3a and 3b for convenience of explanation. Note that signal polarity is displayed from the L1 (secondary winding) point of view.

Figure 4:
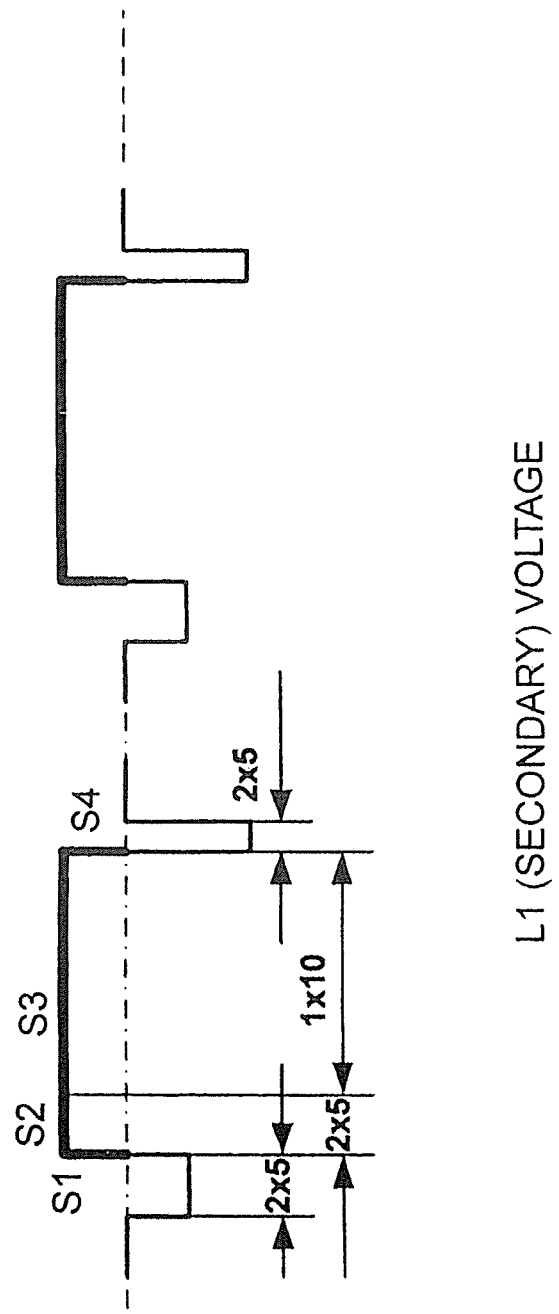
FIG. 4 shows an exemplary waveform of a secondary voltage of one circuit section of FIG. 1.

FIG. 4 shows an exemplary waveform of the secondary voltage (L1) of one circuit section to further illustrate the polarity and relative amplitude for each step in the sequence of the circuit operation. The operation for the various sequenced steps in terms of the poly-phases as described below is identified as follows: "2×5" indicates 5 phases in parallel operation at the time, i.e. first 5 phases, than remaining 5 phases, then the initial 5 phases, and so on; and "1×10" indicates operation of all 10 phases, such as sequentially with partial overlap or with no overlap.

Figure 5:
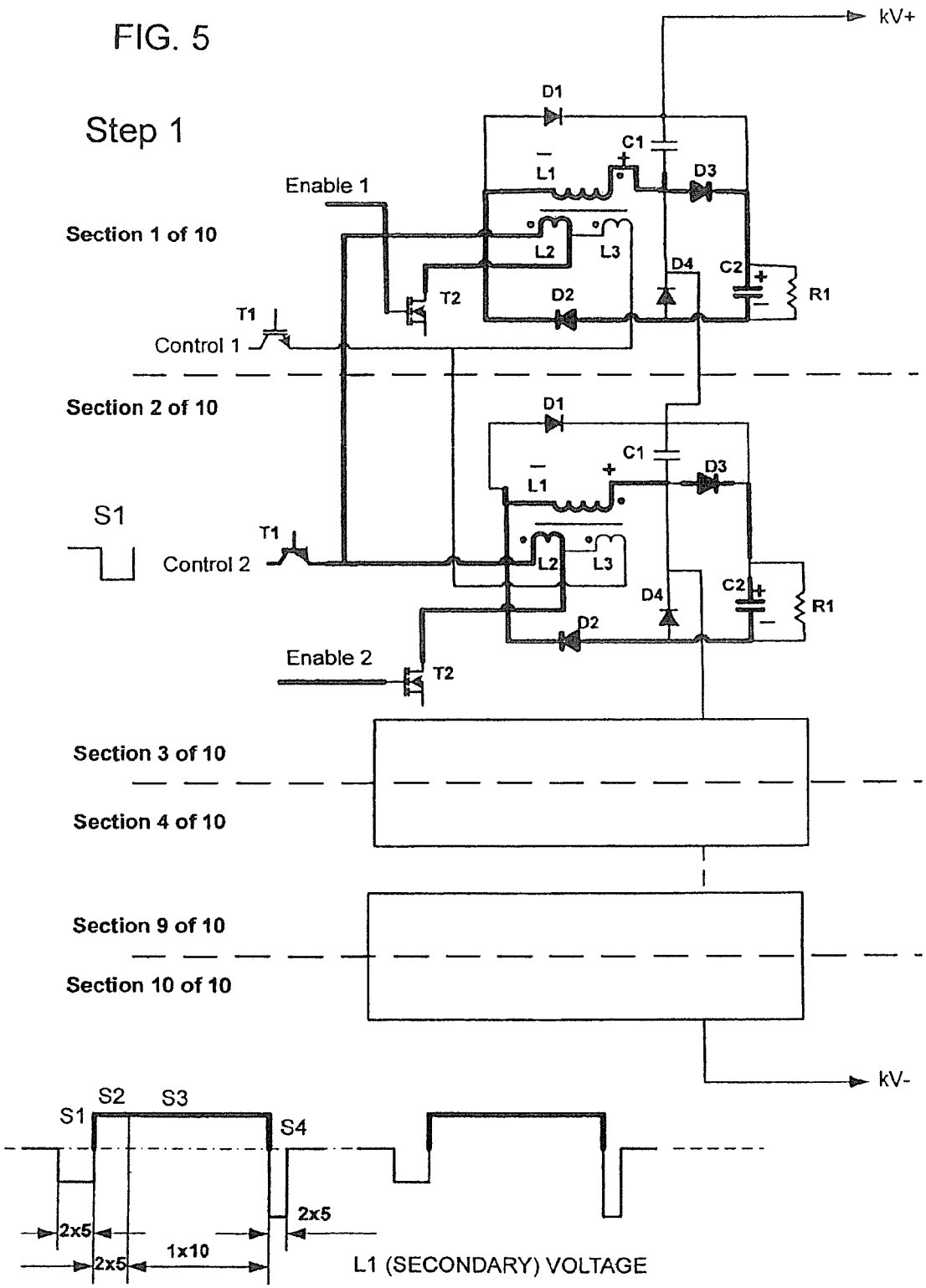
FIG. 5 shows a schematic diagram of FIG. 3 emphasizing the current path in step 1 of the circuit operation.

Turning to FIG. 5, an initial step of operation to charge capacitor C2, step 1, is now described. Components participating in that step of operation are marked in thick (versus thin lines for components less actively participating in a given step, e.g. reverse biased rectifiers). The description is made in terms of circuit sections 1 and 2, and equally applies to all 10 sections (i.e. sections 3/4, 5/6, 7/8, and 9/10). The sequence of operation is as follows: Transistor T2 in Sections 1-10 is enabled. A stream of short negative pulses is applied to the control 2 (T1 on Section 2), polarity is described from the point of view of L1. The impulses are produced by energizing together up to 5 phases in sequence of the poly-phase transformer connected in parallel via the corresponding enabling transistor T2, such as, for example phases 1-5 and then phases 6-10. These sections can be energized in sequence: first 5, second 5, first 5, etc. One suitable (exemplary) frequency for the control pulse stream is 250 kHz (period 4 microseconds) with the duration of individual pulse about 1 microsecond; this sequence energizes primary winding L2 as well as secondary winding L1 with the polarity as indicated on the FIG. 5. Current flows through L1, D3, C2, and D2 (rectifiers D1, and D4 are back-biased and not conducting). Capacitor C2 is charged with polarity indicated on FIG. 5 thus providing a fast charging of C2. The operation of step 1 typically takes place before any x-ray exposure request has been made, and is done to bring circuitry in the initial state. Step 1 operation is not time critical operation and does not affect the rise time or fall time of the x-ray impulse.

Figure 6:
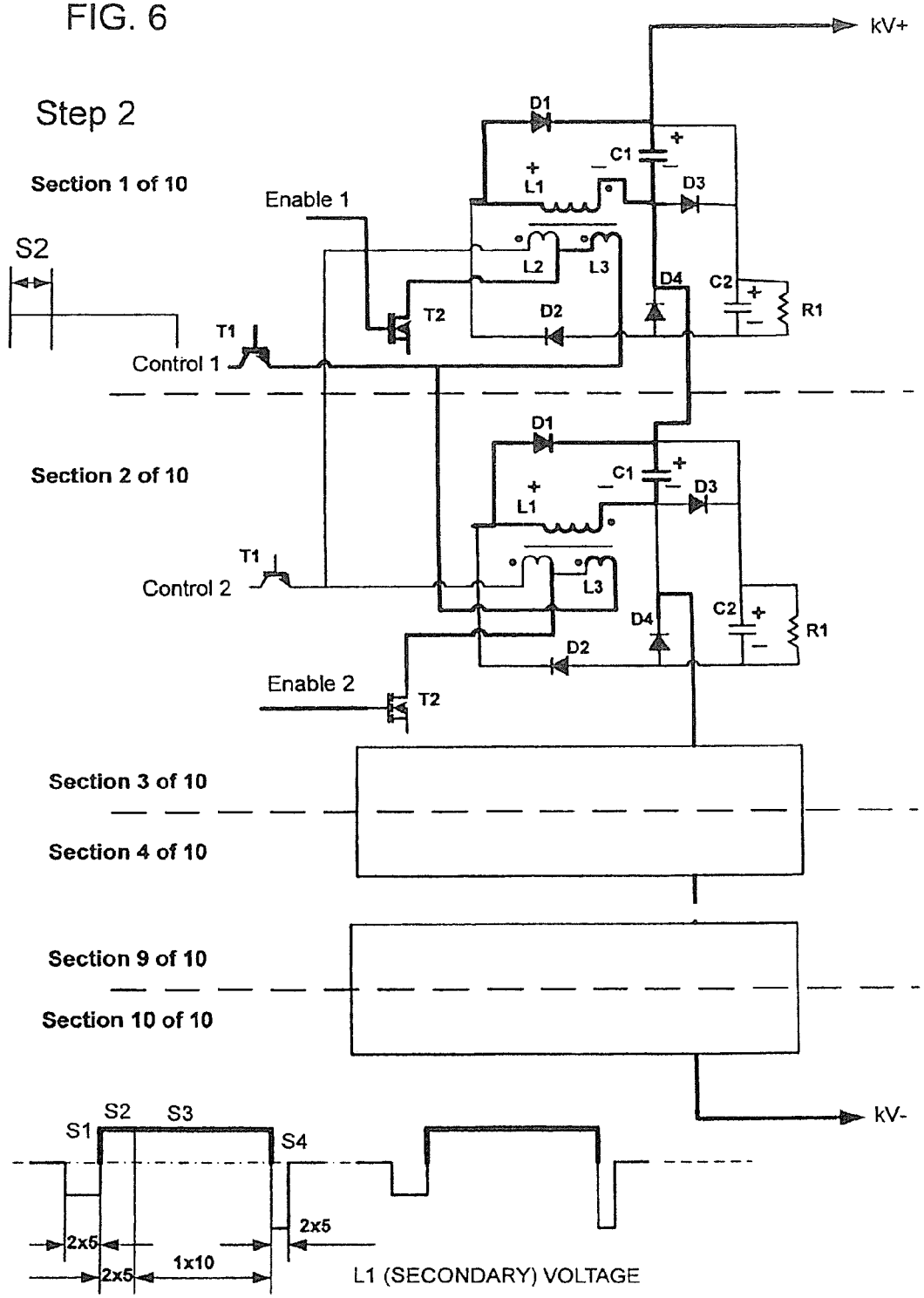
FIG. 6 shows a schematic diagram of FIG. 3 emphasizing the current path in step 2 of the circuit operation.

Turning to FIG. 6, a step to form the shape of fast rise time front edge of the x-ray impulse, step 2, is now described. The sequence of operation is as follows: Transistor T1 in Sections 1, 3, 5, 7, and 9 is enabled. A stream of short positive pulses applied to the Control 2 (T1 on Section 2), the polarity is described from the point of view of L1. The impulse is produced by energizing together up to 5 phases in sequence of the poly-phase transformer (thus, the windings are effectively connected in parallel), such as for example 1-5 and then 6-10. The goal is to provide maximum energy in the shortest period of time. During step 2, the system operates practically as a two phase system, thus producing a higher ripple level. However, because the high voltage is on the rise during step 2 (the continuously changing voltage of the leading edge of the x-ray impulse), there is no negative impact experienced from the higher ripple levels during a step 2 operation. The sections are energized in sequence: first 5, second 5, first 5, etc., one suitable (exemplary) frequency of the control pulse stream is 250 kHz (period 4 microseconds) with the duration of individual pulse about 1 microsecond, the purpose of such sequencing is to produce most energetic start to shape fast rise time of the x-ray impulse. This sequence energizes primary winding L3 and secondary winding L1 energized with the polarity indicated on the FIG. 6. Current flows through L1, D1, and C1 (rectifiers D2, D3, and D4 are back-biased). Capacitor C1 is charged with polarity indicated on FIG. 6. This step provides a relatively high energy transfer to fast charge C1 and to form the fast rise time of the x-ray impulse.

Figure 7:
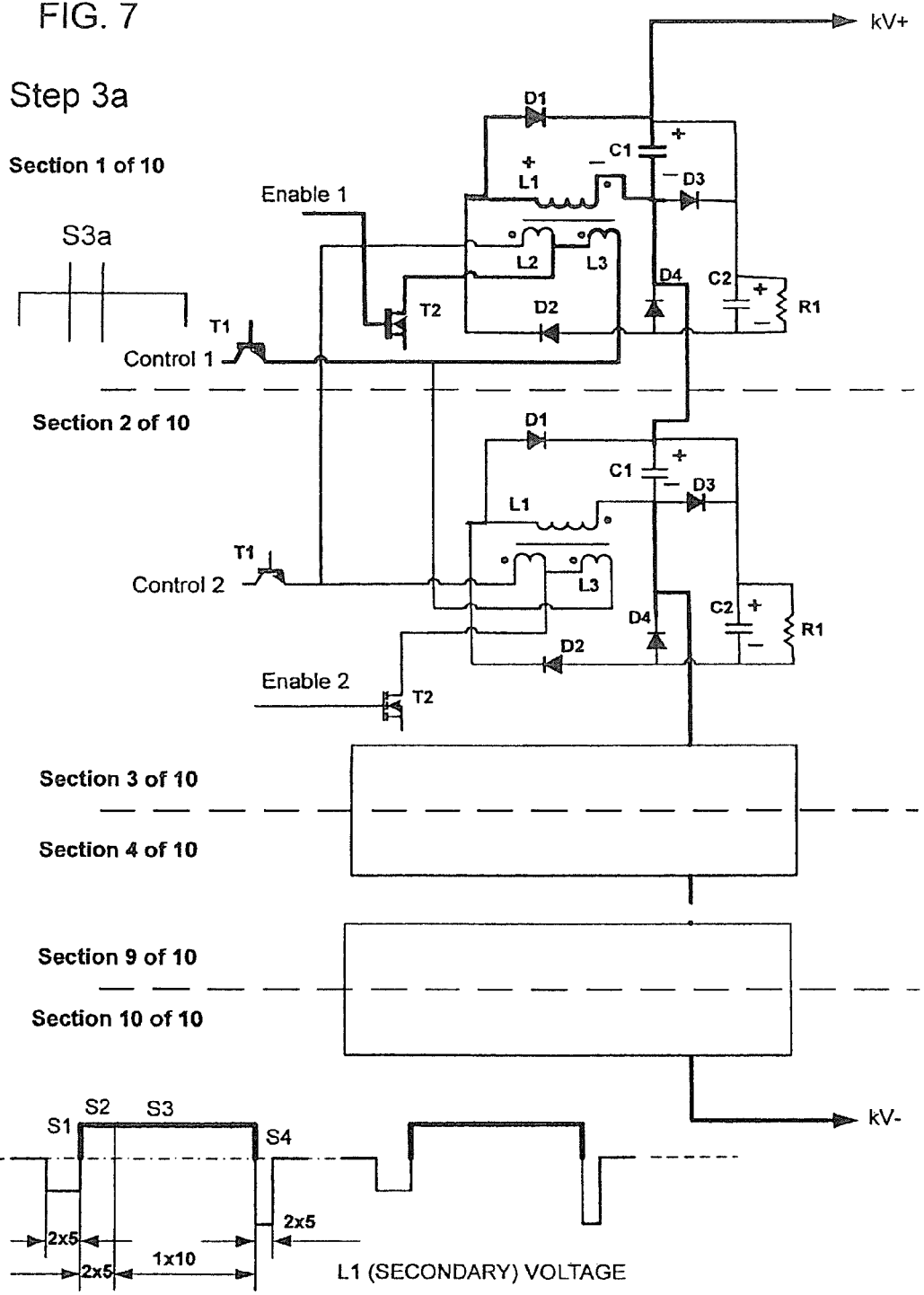
FIG. 7 shows a schematic diagram of FIG. 3 emphasizing the current path in step 3a of the circuit operation.

Turning to FIG. 7, a step to form a low ripple amplitude flat-top of an x-ray impulse, step 3a, is now described. The sequence of operation is as follows: Transistor T1 in Section 1 is enabled. A stream of short positive pulses applied to the Control 2 (T1 on Section 2) with a polarity described from the point of view of L1, Section 1, thus energizing phase 1 of the poly-phase transformer, energizing primary winding L3, section 1 and secondary winding L1 with a polarity as indicated on the FIG. 7. Current flows through L1, D1, and C1 in section 1, thus maintaining charge of capacitor C1, section 1 with a polarity as indicated on the FIG. 7, while under the load of the operational x-ray tube (note that rectifiers D2, D3, and D4 are back-biased). This sequence is repeated through all sections (all phases) of the poly-phase transformer in phase sequence.

Figure 8:
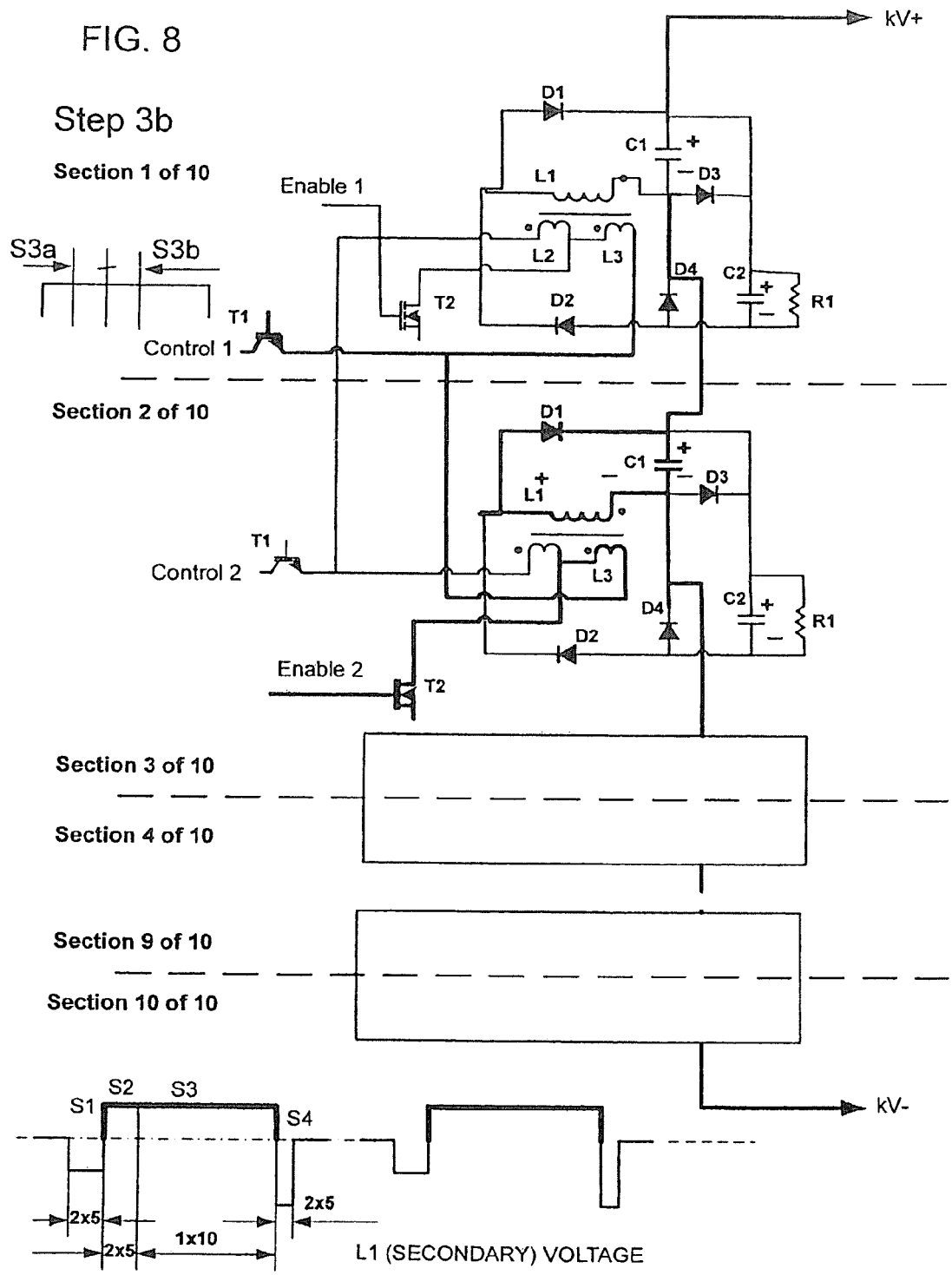
FIG. 8 shows a schematic diagram of FIG. 3 emphasizing the current path in step 3b of the circuit operation.

Turning to FIG. 8, a step to form a low ripple amplitude flat-top of an x-ray impulse, step 3b (a continuation of step 3a), is now described. The sequence of operation is as follows: Transistor T1 of section 1 is enabled. The Enable 2 signal is also provided to T2, section 2. A stream of short positive pulses is applied to the Control 1 (T1 on Section 1) with a polarity as described from the point of view of L1, Section 2. These impulses are produced by energizing phase 2 of poly-phase transformer, thus energizing primary winding L3, section 2 and secondary winding L1 with a polarity as indicated on FIG. 8. Current flows through L1, D1, and C1 in section 2 charging capacitor C1, section 2 with a polarity as indicated on FIG. 8 (note that rectifiers D2, D3, and D4 are back-biased). This sequence can be repeated through remaining sections of poly-phase transformer and steps 3a and 3b can be repeated as long as necessary to achieve a desired pulse width of the x-ray impulse. Note that a step 3 (a, b, etc) is a typical operation for the polyphase transformer which engages all phases in sequence thus yields all of the benefits of poly-phase operation to form and maintain a substantially constant level of x-ray impulse high voltage (the x-ray impulse "flat-top") with a minimal amount or ripples at the highest operating frequency.

Now, turning to FIG. 9, a step to form the fast fall time of the x-ray impulse, step 4, is now described. This step is performed after the x-ray high voltage has been turned off and storage capacitors C1 must be discharged under no load to form a falling edge of the x-ray impulse. The sequence of operation is as follows: Transistors T2 in Sections 1-10 is enabled. A stream of short negative pulses is applied to the Control 2 (T1 on Section 2). The polarity is shown from the point of view of L1. This pulse is more energetic (higher amplitude) than the pulse of step 1 as described above. The x-ray impulse is produced by energizing together up to 5 phases in sequence of the poly-phase transformer connected in parallel (e.g. 1-5 and then 6-10) and the phases and sections can be energized in the following sequence: first 5, second 5, first 5, etc. An exemplary frequency suitable for this pulse stream is about 250 kHz (period 4 microseconds) with the duration of individual pulse about 1 microsecond. Using this sequence, primary windings L2 in all 10 phases and secondary windings L1 are energized with a polarity as indicated on FIG. 9. Current flows through L1, C1, C2, and D2 (note that diodes D1, D3, and D4 are back-biased). Capacitor C1 is forcefully discharged with a polarity opposite to that indicated on FIG. 9. This step provides a fast energetic discharge of C1, therefore causing the fast fall time of the x-ray impulse.

Turning to FIG. 10, a step to discharge capacitor C2, step 5, is now described. The sequence of operation is as follows: Transistors T1 and T2 in Sections 1-10 are disabled. Capacitor C2 is discharged through shunt resistor R1 (not a time critical operation). Capacitor C2 can also be still partially charged when the new cycle started from Phase 1 is initiated. Any such partial charge, remaining on C2 from a previous x-ray impulse, can assist in a following step 1, when preparation begins for generation of another x-ray impulse.

Therefore, it can be seen that in poly-phase operation, the sequential operation of the circuit as described above in part I and part II causes the charge and discharge of capacitors C1 and C2 (e.g. FIG. 3) in a pre-defined way, and provides the desired forward-biasing and back-biasing of diodes D1-D4 to create certain current paths as described in detail above. While useful as a single section, such as in single phase operation, the most advantageous benefits, including fast rise time, fast fall time, and a low amplitude ripple flat-top x-ray impulse, is achieved with multiple sections in a poly-phase configuration (part II and FIG. 19).

The poly-phase operation described in Part II above is now summarized in slightly more detail as follows:

In step 1, capacitor C2 is pre-charged (i.e. C2 is charged before an x-ray impulse is called for). This action is not time critical and can generally occur prior to an x-ray exposure command. Several phases of a poly-phase transformer in parallel can deliver this boost of energy to capacitor C2. Note that C2 functions later in forming the sharp fall time at the end of this cycle.

In step 2, the shaping of the front edge of the x-ray impulse, capacitor C1 is charged. A relatively large amount of energy is forced into capacitor C1 in a relatively short period of time (microseconds). Several phases of the poly-phase transformer used in parallel can deliver this boost of energy. The operation of step 2 contributes to shortening the rise time of the x-ray impulse. Because phases working in parallel do not create multi-phase ripple, ripple is increased during step 2, however low ripple is irrelevant during the x-ray impulse rise time.

In steps 3a, 3b, 3c, 3d . . . 3j (for 10 pulse operation), the flat-top of the x-ray impulse is formed. Here, where low ripple is desired, each phase of the poly-phase transformer operates in sequencing with an appropriate overlap. Each phase maintains its own HV capacitor C1 charged under load to a desired voltage. A sum voltage (the sum of n-sections output voltage) on the end of the C1 chain creates a desired kilovolt ("kV") across the terminals of the x-ray tube being powered. Each phase provides the appropriate phase shift that creates the relatively high ripple frequency during the flat-top of the x-ray impulse.

In step 4, the relatively fast falling edge of the x-ray impulse is formed. The control impulses during this phase force the expeditious discharge of C1 while additionally charging C2. In phase 4, as in Phases 1 and 2, parallel phases are used to force energy into the capacitors, thus causing the shortening of the x-ray impulse fall time over prior art techniques. Back-biased diode D3 facilitates the closed circuit loop that includes C1 and C2.

Having described poly-phase operation, it can now be appreciated that one or more sections of either of the circuit topologies shown in FIG. 1 or FIG. 2 can also be used in single phase applications (typically a single section). One difference in operation is that in single section operation there will not be overlapping phases available to increase the ripple frequency during an x-ray impulse flat-top. Also, in single phase operation, there will not be the (effective) parallel combination of phases 2×5 or 1×10.

Part III, Fast Pulse Rectifier with Energy Reuse:

As previously noted another problem with prior art x-ray generators is that stored energy is typically damped through discharge components and converted to heat. In the active rectifier section described below, the circuit section reuses energy to provide fast charge or discharge process, effectively producing fast rise and fall edges of HV impulses. Following a detailed description of the operation of a single circuit section of this embodiment of fast pulse rectifier, a poly-phase version of the circuit is described.

Figure 11:
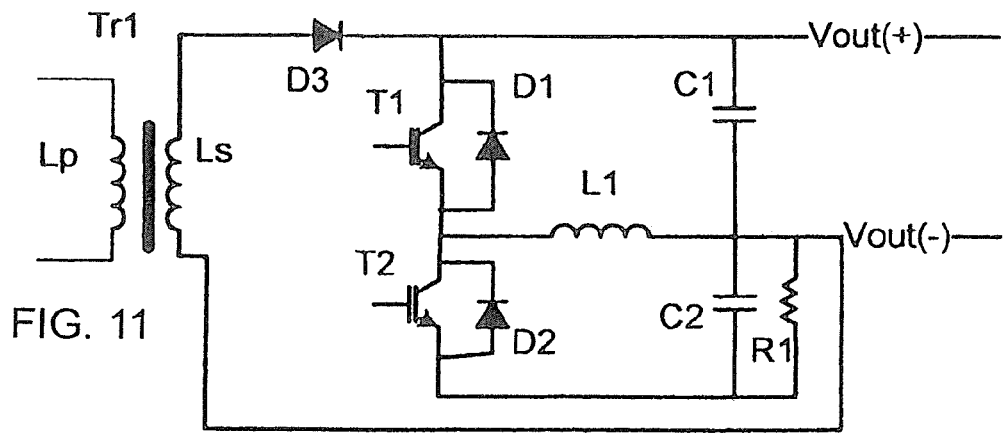
FIG. 11 shows a schematic diagram of one exemplary embodiment of a single section (single phase) of an active charge-discharge circuit.
Figure 12:
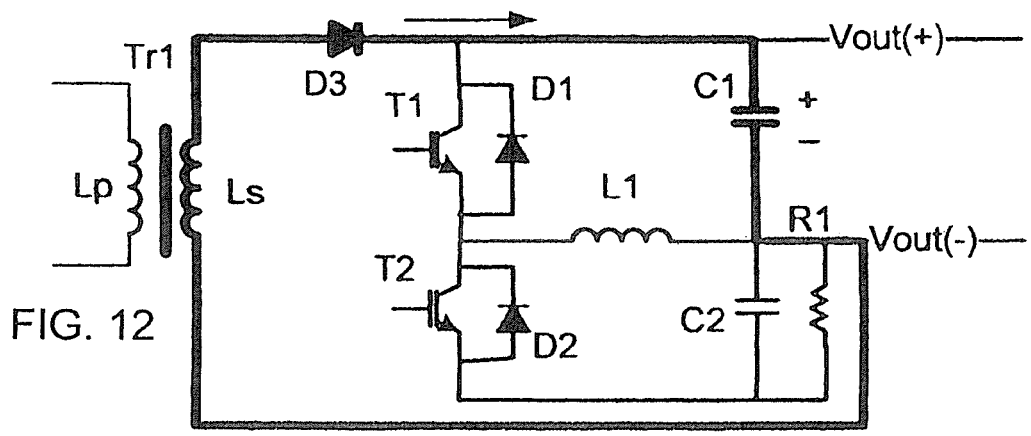
FIG. 12 shows a schematic diagram illustrating a first cycle of circuit operation.

FIG. 11 shows a schematic diagram of one exemplary embodiment of a single section (single phase) of an active charge-discharge circuit. The following is a list of the circuit components of FIG. 11:

Tr1—One phase of poly-phase transformer
Lp—Primary winding
Ls—Secondary winding
T1, T2—Switching transistors
D1, D2—By-pass rectifiers (typically diodes)
D3—Rectifier (typically a diode)
L1—Inductor
C1—Main HV capacitor
C2—Recharging capacitor
R1—Shunt resistor Now turning to FIG. 12, a first cycle of circuit operation is described. The first cycle starts by producing a HV pulse via Tr1. The HV pulse is rectified by D3 causing charging of C1 with a voltage polarity as indicated in FIG. 12. Note that C2 continuously slowly discharges via R1 with the discharge constant ($\tau$) R1C2.

Figure 13:
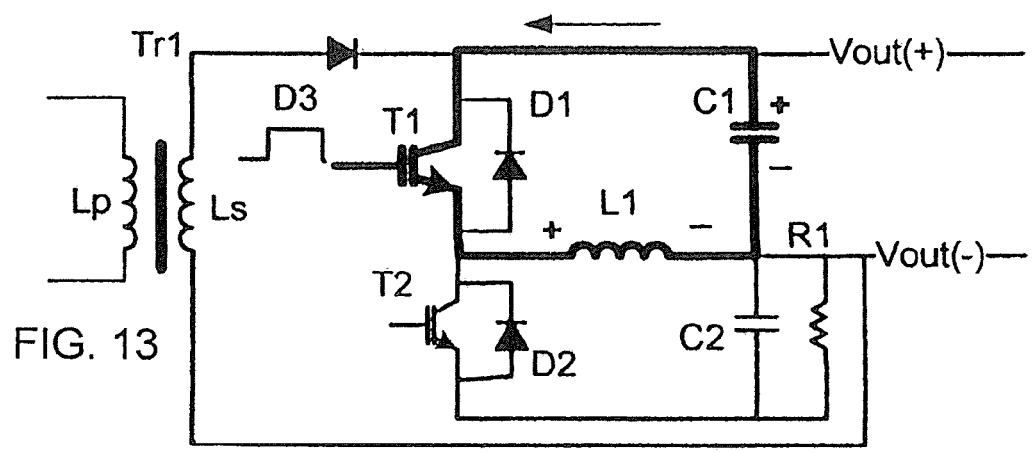
FIG. 13 shows a schematic diagram illustrating a second cycle of circuit operation.

FIG. 13 shows the second cycle of operation. The second cycle starts with gating T1 ON. Gating T1 ON causes C1 to discharge through T1 and the charging of L1 with a polarity as indicated on FIG. 13. This second cycle of operation causes a discharging of the HV filter capacitor and assists in shaping sharp falling edge of the HV pulse.

Figure 14:
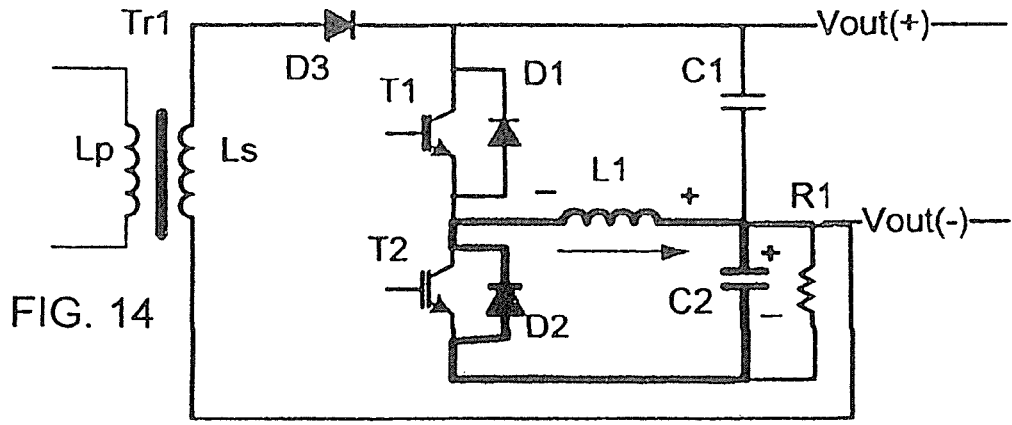
FIG. 14 shows a schematic diagram illustrating a third cycle of circuit operation.

FIG. 14 shows the third cycle of operation. In the third cycle L1 attempts to sustain a discharge current via C2 and D2. The discharge current re-charges C2. Note that the charging circuit consists of L1, C2, and D2.

Figure 15:
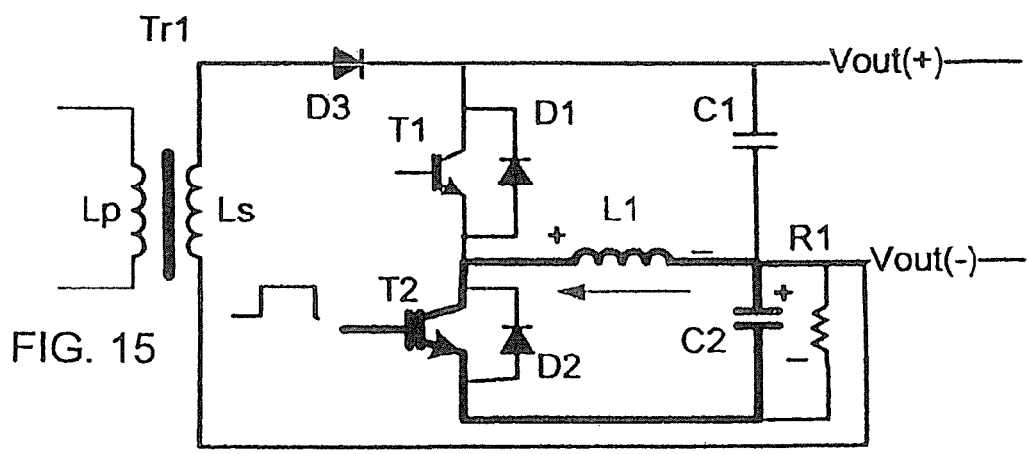
FIG. 15 shows a schematic diagram illustrating a fourth cycle of circuit operation.

FIG. 15 shows the fourth cycle of operation. The fourth cycle begins by gating T2 ON. Gating T2 ON causes energy stored in C2 to be transferred to L1 via the chain C2, L1, and T2.

Figure 16:
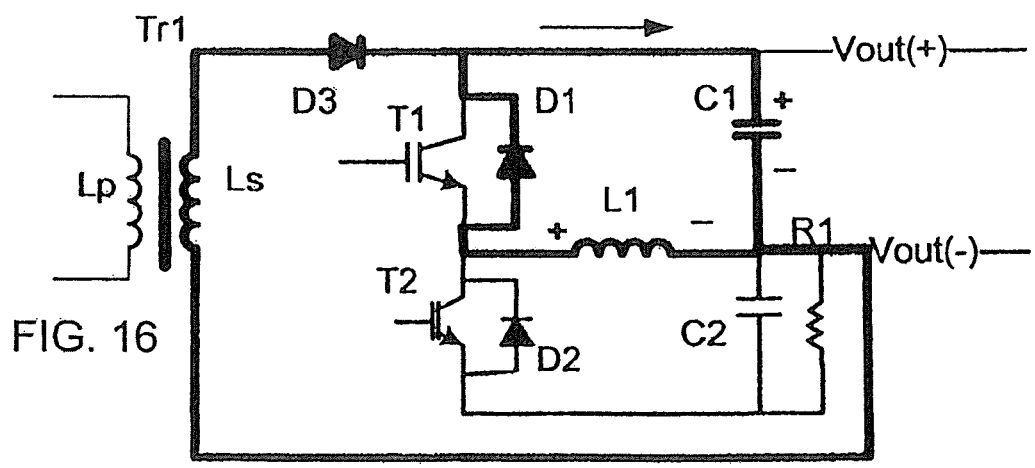
FIG. 16 shows a schematic diagram illustrating a fifth cycle of circuit operation.

FIG. 16 shows the fifth cycle of operation. In the fifth and final cycle, high voltage applied to Tr1 causes C1 to charge via L1. This process acts to charge the HV filter capacitor and assists in shaping sharp rising edge of the HV pulse. As a result of the five cycles of operation described above, energy is transferred back and forth with only a negligible wasteful transfer of energy to heat, such as where resistor R1 serves as a final discharge route of C1 and C2 after production of HV pulses has stopped.

FIG. 17 shows a schematic diagram of a poly-phase transformer design using multiple circuit sections labeled Phase 1 to Phase N, useful for poly-phase operation.

Figure 18:
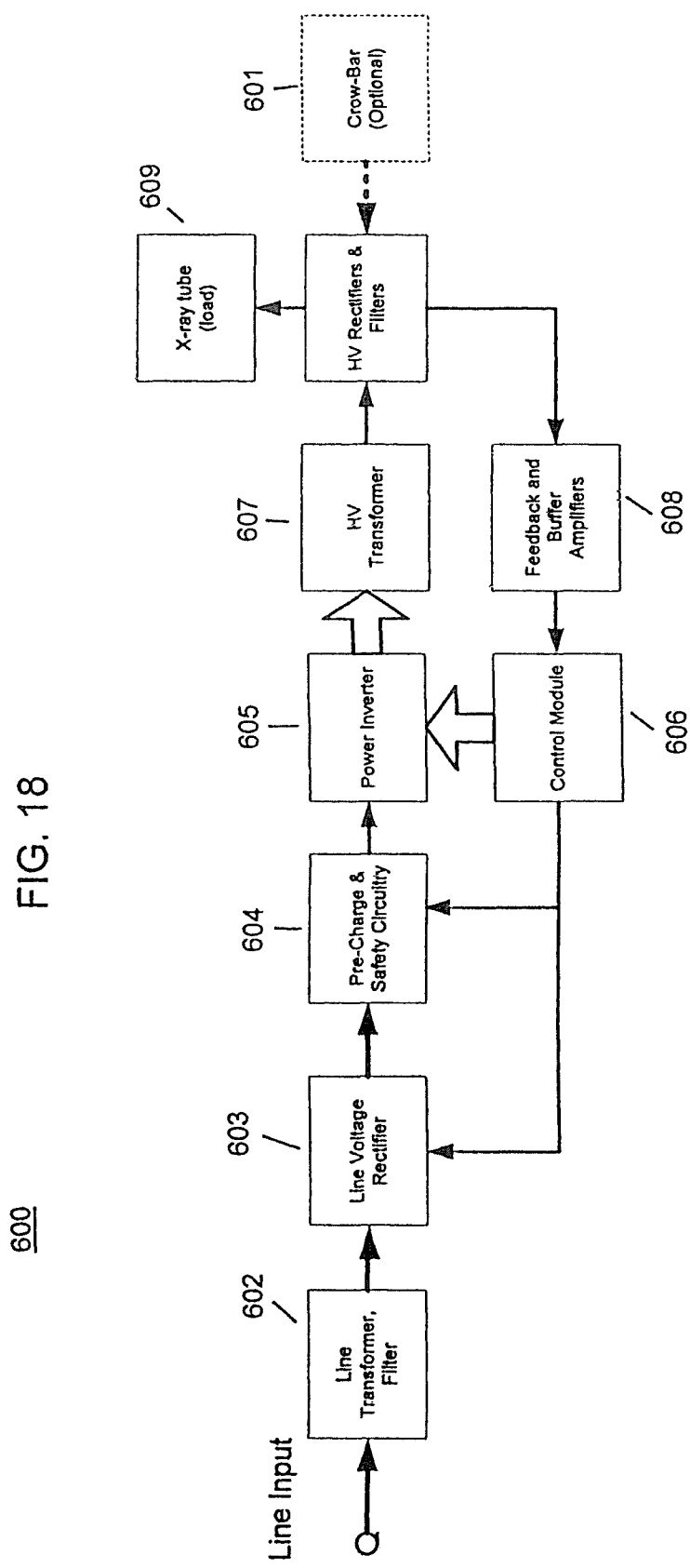
FIG. 18 shows a block diagram of one embodiment of a conventional x-ray generator.

Part IV, X-Ray Generators and Other Applications:

FIG. 18 shows a block diagram of one embodiment of a conventional x-ray generator 600. Typically, an x-ray apparatus has a line transformer and line filter 602 where a connection is made to the electrical mains of a building, such as those in a hospital. The transformer provides some electrical safety by electrical isolation and the filter can eliminate some undesired interference signals present at the mains connection. In some cases, a transformer also provides a matching voltage for the generator. A line rectifier 603 can be used to rectify the line power from line transformer and line filter 602 to provide one or more DC rails to operate various circuit components of the x-ray apparatus. Pre-charge and safety circuitry 604 can enhance radiation safety by providing important safety interlock and x-ray generator inhibit/enable operations. Such interlocks can range from cabinet door safety interlocks to software generated interlocks for computer control of the x-ray apparatus. Pre-charge and safety circuitry 604 can also react to feedback signals, such as signals indicating x-ray energy and/or time duration of x-ray impulses. Power inverter 605 in conjunction with HV transformer 607 and HV rectifiers and filters 610 can be used to generate the x-ray impulse that creates a desired high voltage to power x-ray tube 609 (the electrical load for the x-ray generator). The amplitude and/or duration of the x-ray impulse can be controlled, for example, by feedback and buffer amplifiers 608 in conjunction with a control module 606. As previously discussed, typical prior art x-ray apparatus employ a "crowbar" circuit 601 to speed the fall time of the x-ray impulse. Or, in other prior art x-ray generators, fast fall times are difficult to achieve because there are no active components involved to turn off an x-ray impulse and there is only passive discharging governed by RC constants of circuitry. By contrast, a poly-phase design has an inherently better performance in shaping edges of the pulses due to significantly smaller filtering capacitance.

Figure 19:
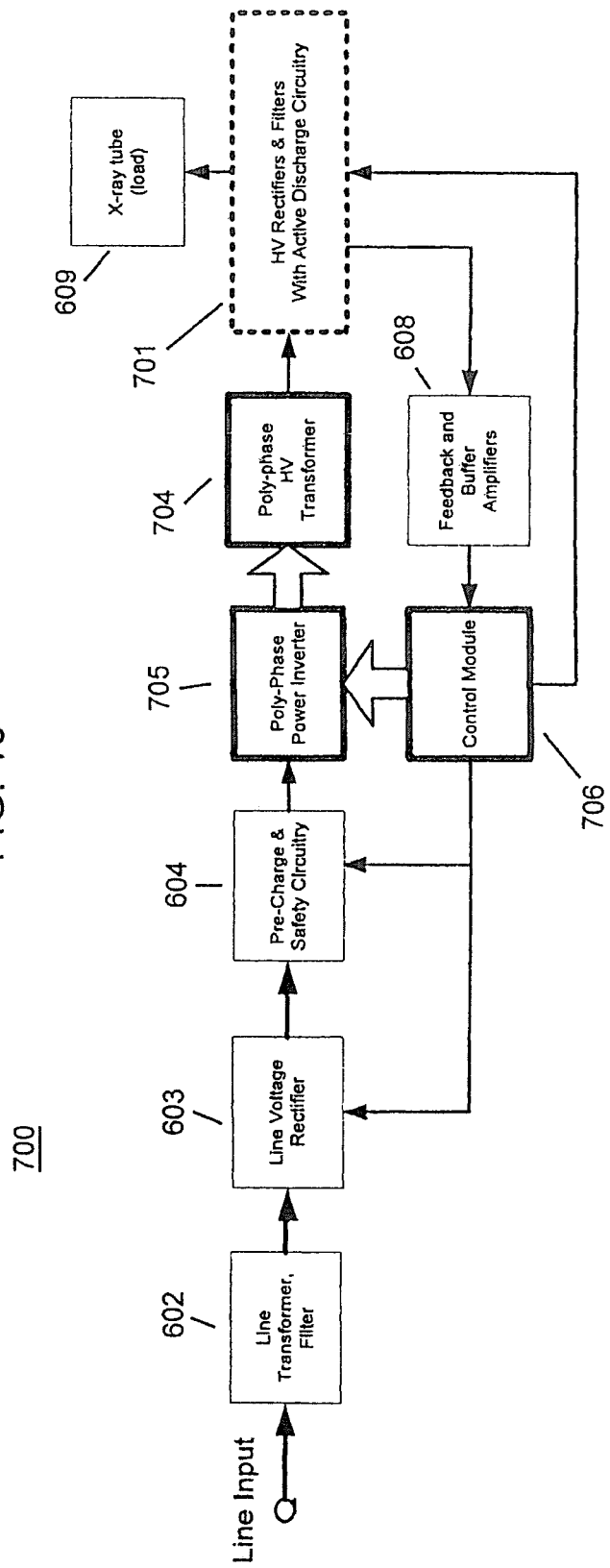
FIG. 19 shows a block diagram of one embodiment of an x-ray generator having a poly-phase x-ray generator using multiple sections of the new fast pulse circuit topologies described herein.

FIG. 19 shows a block diagram of one embodiment of an x-ray generator 700 using a poly-phase x-ray generator using multiple sections of the new circuit topology described herein. Some of the functional blocks, e.g. line transformer and line filter 602, line rectifier 603, feedback and buffer amplifiers 608, and x-ray tube 609 can be of conventional design. The new blocks poly-phase inverter 705, poly-phase HV transformer, and control module 706 have been described in part in co-pending U.S. patent application Ser. No. 12/275, 679, which has been incorporated herein in its entirety. The new block HV rectifiers and filters with active discharge circuitry 701 includes the new circuit topology described herein, particularly as described in section II. One purpose of the block diagram of FIG. 19 is to draw analogy to a conventional x-ray apparatus. However, there are some differences, even at this block diagram overview level. For example, note that there is some overlap of the blocks in FIG. 19, since for example, the new circuit topology as described above includes the windings of the poly-phase HV transformer 704. Also, as described above, the operation of control module 706 and/or poly-phase power inverter 705 is modified to cause the various modes of operation of the various steps (e.g. steps 1-5) in poly-phase operation. Such sequencing of steps in poly-phase operation includes shifting in the range from substantially "in-phase operation" (e.g. "1×5" in step 1 and step 4, FIG. 4) to full poly-phase operation (e.g. "1×10" in steps 3 and step 3b, FIG. 4).

Thus it can be seen that the new circuit topologies described herein for use in x-ray generators, particularly in poly-phase embodiments, offer advantages of low ripple levels, fast switching times, and the ability to shape power impulses to substantially eliminate over-shoot and under-shoot. Such x-ray generators are particularly well suited for use in applications including, dual energy applications, tomosynthesis applications, low dose CT applications, and improved Pulsed Fluoro due to shorter available pulse widths and better control of patient doses due to the substantial elimination of soft radiation. Overall benefits include low stored energy, simplified coil designs, less demand on power switching components, a ripple frequency that is less dependent on requested power levels, a compact design due to the absence of large HV Capacitors, better EMI suppression due to the high emission frequency, and a wider dynamic range and precision of power regulation.

Other applications for the new circuit topologies described herein, include high performance general purpose power supplies, where advantages include low ripple levels, low stored energy, less demand on power switching components, a ripple frequency which is substantially independent of a requested power level, a compact design due to an absence of large filter capacitors, easier EMI shielding due to high emission frequency ~1 MHz, a wide range of power regulation, precision in power regulation, fast start up time for appliances such as TVs, Stoves, etc. and a suitability for use in battery charging.

Special purpose power supplies, such as those used for LASERs (e.g. for LASER control) and RADAR (e.g. for RADAR control) can also benefit from the advantages of the new circuit topologies described herein. Such advantages include low stored energy, high switching rate, precision in power regulation, an ability to handle fast variation of load, suitability to provide short powerful strobes, low EMI emission, an improved regulation of the output power, the ability to maintain constant power and a suitability to provide multiple outputs isolated power supplies.

Power signal generators can also benefit from the ability of the new circuit topologies described herein to shape power impulses and the ability to produce DC or AC power at any predefined frequency including FM (frequency modulation). Another application for the new circuit topologies described herein includes power signal modulators, such as power signal modulators used for communication by high power means (including communication by RADAR, LASERs, radio stations, and power distribution lines) and underwater high power magneto-stricter communication devices. Other applications for the new circuit topologies described herein include power supplies for industrial applications, such as those used in LASER cutting machinery, as sources of power for engines requiring a fast acceleration time (e.g. race cars, and police cars, and other fast acceleration time military applications), and power supplies for high intensity geological acoustic devices. Other medical applications for the new circuit topologies described herein include defibrillators, gamma cameras, radiation therapy devices, MRI gradient amplifiers, and LASER surgery. Poly-phase and multi-axis motor controller applications for the new circuit topologies described herein include stepping motor controllers, multi-phase AC motor controllers, DC motor controllers, and multi-axis motor controllers. Still other applications for the new circuit topologies described herein include audio amplifier applications (e.g. acoustic surrounding amplifiers, surround sound amplifiers, multiple audio speaker controllers), audio effects generators and video equipment controllers such as including multiple video source controllers and visual effect generators.

Part V Summary:

The various embodiments of the new circuit topologies that have been described herein in parts I, II, and III, especially the poly-phase embodiments of part II and part III, can be used in an x-ray generator to generate an x-ray impulse having sharp rising and falling edges, such as the exemplary x-ray apparatus as described in part IV. The sharp rising and falling edges of the new circuit topology can be an order of magnitude faster or more than has been achieved over "crowbar" circuit technologies of the prior art. Another aspect of a new active rectifier section for use in x-ray generators, suitable for use in an x-ray apparatus was described in part III.

The term "rectifier" as used herein includes any suitable electronic component that conducts current for one direction of applied voltage and does not conduct current for the opposite reversed voltage, or to any component that can be so-configured. The definition of rectifier as used herein includes a synchronously switched component that conducts in only one direction by virtue of when the component is switched ON or OFF in time, in this application, generally in synchronization with a pulse stream and/or a phase of a poly-phase transformer. While in the most basic embodiments the rectifiers are typically diodes, one or more of the rectifiers can alternatively be an active component, such as a silicon controlled rectifier ("SCR") or other suitable switch electronic switches such as a metal oxide field effect transistor ("MOSFET"), an insulated gate bipolar transistor ("IGBT"), among others.

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

While the present invention has been particularly shown and described with reference to the preferred mode as illustrated in the drawings, it will be understood by one skilled in the art that various changes in detail may be affected therein without departing from the intended scope of the invention according to the following claims.

The invention claimed is:

1. An X-ray generator for generating a fast rise-time pulse, said generator comprising:
    a n-phase poly-phase transformer having at least one primary winding and at least one secondary winding per phase;
    n rectifier circuits, each one of said n rectifier circuits being electrically coupled to each of said at least one secondary winding per phase, each of said n rectifier circuits comprising at least a first capacitor electrically coupled to at least a first rectifier, said first rectifier electrically disposed between said at least one secondary winding and said first capacitor and configured to provide a fast rise time of a leading edge of a fast rise-time pulse, and at least a second capacitor electrically coupled to at least a second rectifier, said second rectifier being electrically disposed between said at least one secondary winding and said second capacitor configured to provide a filtered n-phase pulse flat-top; and
    at least n active control switches, each of said active control switches being electrically coupled to at least one of said primary winding and configured to set a selected one of rectifier mode: 1) a fast pulse rise-time mode and 2) a flat-top low ripple mode, and
    wherein each of said first capacitors is charged by a rectified phase ripple of less than n at or before a leading edge of said fast rise-time pulse, and each of said second capacitors is configured to operate with an n-phase ripple to provide a substantially flat top of said fast rise-time pulse.

2. The x-ray generator according to claim 1, wherein each of said first capacitor and said second capacitor are pre-charged before the leading edge of said fast rise-time pulse.

3. The x-ray generator according to claim 1, wherein a peak pulse amplitude of said fast rise-time pulse is generated by a series combination of a plurality of rectified voltages, each one of said plurality of rectified voltages being output from each of said n-rectifiers.

4. A method for generating a fast rise-time X-ray pulse, said method comprising:
  providing an n-phase x-ray generator, said generator including an n-phase transformer having at least one primary winding and at least one secondary winding per phase;
  providing n sections of rectifiers, each rectifier having at least a fast pulse rise-time mode and a n-phase ripple flat-top mode;
  charging at least a first capacitor in each of said n sections of rectifiers at a ripple of less than n-phases to create a fast leading edge of said fast rise-time X-ray pulse; and
  charging at least a second capacitor in each of said n sections at an n-phase ripple to create a substantially flat-top of said fast rise-time X-ray pulse.

5. The method according to claim 4, further comprising pre-charging said first capacitor prior to the act of charging said first capacitor.

6. The method according to claim 4, further comprising pre-charging said second capacitor prior to the act of charging the first capacitor.

7. The method according to claim 4, further comprising discharging said first capacitor to create a fast fall time of a falling edge of said fast rise-time pulse prior to said act of charging at least the second capacitor.

8. The method according to claim 4, further comprising discharging said second capacitor prior to said act of charging at least the second capacitor.

* * * * *